(12) United States Patent
Von Nussbaum et al.

(10) Patent No.: US 7,737,120 B2
(45) Date of Patent: Jun. 15, 2010

(54) METHODS FOR THE SPECIFIC PREPARATION OF LYSOBACTIN FRAGMENTS

(75) Inventors: Franz Von Nussbaum, Duesseldorf (DE); Werner Schroeder, Wuppertal (DE); Chantal Fuerstner, Muelheim An der Ruhr (DE)

(73) Assignee: Aicuris GmbH & Co. KG, Wuppertal (DE)

( * ) Notice: Subject to any disclaimer, the term of this patent is extended or adjusted under 35 U.S.C. 154(b) by 496 days.

(21) Appl. No.: 11/800,102

(22) Filed: May 4, 2007

(65) Prior Publication Data

US 2008/0021199 A1 Jan. 24, 2008
US 2009/0105448 A2 Apr. 23, 2009

Related U.S. Application Data

(63) Continuation of application No. PCT/EP2005/011364, filed on Oct. 22, 2005.

(30) Foreign Application Priority Data

Nov. 5, 2004 (DE) ....................... 10 2004 053 409

(51) Int. Cl.
*A61K 38/08* (2006.01)
*A61K 38/48* (2006.01)

(52) U.S. Cl. ....................... 514/15; 530/328; 424/94.64

(58) Field of Classification Search ....................... None
See application file for complete search history.

(56) References Cited

U.S. PATENT DOCUMENTS 4,754,018 A 6/1988 Tymiak et al.

FOREIGN PATENT DOCUMENTS

WO WO-2004/099239 11/2004

OTHER PUBLICATIONS

O'Sullivan, 1988, Journal of Antibiotics, 41, 1740-1744.*
Blackburn, 1993, Drug Metabolism and Disposition, 21, 573-579.*
Blackburn et al., Drug Metab. Dispos. (1993) 21(4):573-579.
Bonner et al., J. Antibiot. (1988) 41:1745-1751.
Cardillo et al., Eur. J. Org. Chem. (2000) 2489-2494.
International Search Report for PCT/EP2005/011364, Mailed on Jan. 26, 2006, 5 pages.
Palomo et al., Pure Appl. Chem. (2000) 72(9):1763-1768.
Palomo et al., Tetrahedron Letters (2001) 42:8955-8957.
O'Sullivan et al., J. Antibiot. (1988) 41-1740-1744.
Tymiak et al., J. Org. Chem. (1989) 54:1149-1157.
English translation of the International Preliminary Report on Patentability for PCT/EP2005/011364, mailed Jul. 12, 2007, 8 pages.

* cited by examiner

*Primary Examiner*—Andrew D Kosar
*Assistant Examiner*—Satyanarayana R Gudibande
(74) *Attorney, Agent, or Firm*—Morrison & Foerster LLP

(57) ABSTRACT

The invention relates to methods for the targeted production of lysobactin derivatives by combined chemical and enzymatic modifications. In particular, the invention relates to method for preparing lysobactin fragment 4-11 by chemical reduction and cleavage of the resultant product by chymotrypsin.

8 Claims, 2 Drawing Sheets

METHODS FOR THE SPECIFIC PREPARATION OF LYSOBACTIN FRAGMENTS

CROSS-REFERENCE TO RELATED APPLICATIONS

This application is a continuation of pending international application PCT/EP2005/011364, filed Oct. 22, 2005, designating US, which claims priority from German patent application DE 10 2004 053 409.8, filed Nov. 5, 2004. The contents of the above-referenced applications are incorporated herein by this reference in their entirety.

BACKGROUND OF THE INVENTION

The invention relates to methods for the targeted preparation of lysobactin derivatives by combined chemical and enzymatic modifications. In particular, the invention relates to a method for preparing lysobactin fragment 4-11 by chemical reduction and cleavage of the resultant product by chymotrypsin.

Lysobactin is a cyclic depsipeptide which originates from a screening program for finding novel antibiotics acting in the biosynthesis of bacterial cell walls (O'Sullivan J. et al., *J. Antibiot.* (1988) 41(12):1740-1744 and Bonner, D. P. et al., *J. Antibiot.* (1988) 41(12):1745-1751; Tymiak, A. A. et al., *J. Org. Chem.* (1989) 54:1149-1157). It shows strong activity against Gram-positive aerobic and anaerobic bacteria. An unusual feature is the high number of non-proteinogenic amino acids in the molecule. In addition to the three β-hydroxyamino acids (2S,3R)-β-hydroxyleucine, (2S,3R)-β-hydroxyphenylalanine and (2S,3S)-β-hydroxyasparagine, the D-amino acids D-leucine and D-arginine as well as allo-threonine also occur. This complexity and the size of the natural product lysobactin are a great hurdle for targeted chemical modifications.

SUMMARY OF THE INVENTION

It is therefore one object of the present invention to provide novel and alternative synthesis methods for the targeted synthesis of lysobactin fragments in order to make the preparation of novel antibiotics using lysobactin fragments possible.

A solution is offered by targeted enzymatic cleavage, targeted enzymatic production and subsequent linkage of lysobactin fragments in combination with chemical modification steps, for example hydrogenation.

Enzymatic digestion experiments of lysobactin and the open-chain form obtained by hydrolysis ("open-chain lysobactin"; compound of formula (I)) with enzymes such as pepsin, trypsin, chymotrypsin and mucosal peptidase showed no (such as in the case of pepsin, for example) or only inadequate enzymatic digestion (R. A. Blackburn et al., *Drug Metab. Dispos.* (1993) 21(4):573-579). Very slow inefficient enzymatic cleavage of lysobactin occurs only after the opening of the ring by hydrolysis in the buffer used. This leads as an unwanted side reaction to side-chain deamidation at the (2S,3S)-β-hydroxyasparagine. That is the β-hydroxyasparagine unit is converted into a β-hydroxyaspartate unit.

Surprisingly it has been found that the lysobactin fragment 4-11 can be produced highly efficiently and quantitatively by enzymatic cleavage with chymotrypsin from dihydrolysobactin (compound of formula (II)) and octahydrolysobactin (compound of formula (III)) as well as from a mixture of both components. The cleavage takes place so rapidly that the fragments 1-3 and 4-11 are formed virtually after the combination of the reaction partners (substrate and enzyme). Unwanted side reactions in the amino acid side chains do not take place.

(I) R = OH
(II) R = H

-continued (III)

Dihydrolysobactin and octahydrolysobactin are obtained by hydrogenolytic opening of lysobactin with hydrogen, whereby the (2S,3R)-β-hydroxyphenylalanine unit is converted into a phenylalanine or 3-cyclohexylalanine unit. The resulting lysobactin fragments dihydrolysobactin and octahydrolysobactin are then used for the enzymatic digestion.

Surprisingly, dihydrolysobactin and octahydrolysobactin are also good substrates for other enzymes, so that other fragments can also be produced in high yield by selection of the enzyme.

The invention relates to a method for preparing dihydrolysobactin and/or octahydrolysobactin, in which lysobactin is converted to dihydrolysobactin and/or ocatahydrolysobactin by hydrogenolytic ring opening with hydrogen in the presence of a hydrogenation catalyst in a solvent.

Hydrogenation catalysts are, for example, palladium, ruthenium, rhodium, iridium and platinum catalysts, or Raney nickel. These catalysts can be used as salts (for example platinum dioxide, rhodium(III) chloride) or as supported catalysts (for example palladium on carbon (5-30%) or rhodium on carbon (5%)). Suitable support materials for supported catalysts are, for example, activated carbon, kieselguhr, silica gel, bentonites, kaolin, pumice, aluminosilicates or aluminum oxide. A preferred support material is activated carbon.

Bimetallic catalysts or else multicomponent catalysts can also be used.

Preference is given to palladium catalysts, for example palladium on carbon (5-30%), particular preference is given to palladium on carbon (10%).

The hydrogenolytic ring opening generally takes place in a solvent, preferably in a temperature range from room temperature to 150° C., preferably in a temperature range from room temperature to 80° C., in an atmospheric pressure range from atmospheric pressure to 200 bar, preferably in a pressure range from 3 to 80 bar.

Solvents are, for example, alcohols such as methanol, ethanol, or isopropanol, or mixtures of alcohols with water, or acetic acid or aqueous solutions of acetic acid, or THF-water mixtures, or dioxane-water mixtures, or else ternary mixtures of the abovementioned solvents, for example isopropanol-water-acetic acid. Preference is given to an isopropanol-water mixture.

The invention further relates to a method for preparing lysobactin fragment 4-11 and lysobactin fragment 1-3, in which dihydrolysobactin and/or octahydrolysobactin are enzymatically cleaved to give lysobactin fragment 4-11 and lysobactin fragment 1-3.

Preference is given to an enzymatic cleavage of dihydrolysobactin and/or octahydrolysobactin, whereby a eukaryotic serine protease or a microbial serine protease is used as enzyme.

Eukaryotic serine proteases are, for example, chymotrypsin, cathepsin G, chymase or other enzymes of the chymotrypsin family, or other eukaryotic serine proteases which cleave after aromatic amino acids, preference is given to chymotrypsin.

Microbial serine proteases are, for example, subtilisin, proteinase K, Streptomyces protease A or other enzymes which cleave after aromatic amino acids, preference is given to subtilisin.

The invention further relates to a method for the enzymatic cleavage of dihydrolysobactin and/or octahydrolysobactin to give smaller lysobactin fragments.

The invention accordingly further relates to a method for preparing lysobactin fragment 3-11 and/or lysobactin fragment 5-11 and/or lysobactin fragment 4-10 and/or lysobactin fragment 1-9, characterized in that dihydrolysobactin and/or octahydrolysobactin are enzymatically cleaved to give lysobactin fragment 3-11 and/or lysobactin fragment 5-11 and/or lysobactin fragment 4-10 and/or lysobactin fragment 1-9.

Preference is given to an enzymatic cleavage of dihydrolysobactin and/or octahydrolysobactin, whereby a metalloprotease or a cysteine protease is used as enzyme.

Metalloproteases are, for example, thermolysin or mycolysin.

Cysteine proteases are, for example, papain, bromelain or ficin.

The enzymatic cleavage generally takes place in an aqueous cleavage buffer with addition of a $C_1$-$C_4$ alcohol or acetonitrile, preferably in a temperature range from 10° C. to 40° C., preferably in a pH range from 6 to 9 under atmospheric pressure.

An aqueous cleavage buffer contains, for example, ammonium hydrogencarbonate and urea, or sodium phosphate, cysteine and EDTA, or sodium tetraborate, or other additives with which a buffering range of pH 6 to 9 is covered, preference is given to ammonium hydrogencarbonate and urea.

The $C_1$-$C_4$ alcohol is, for example, methanol, ethanol or isopropanol, preference is given to methanol.

Particularly preferably, the enzymatic cleavage takes place in a temperature range from 30° C. to 37° C.

The alcohol concentration in the reaction medium is 0% to 40%, preferably 10% to 15%.

The ratio of enzyme to substrate (dihydrolysobactin and/or octahydrolysobactin) is 1:1 to 1:4000, preferably 1:25 to 1:100.

The invention further relates to the use of lysobactin fragment 4-11 for the synthesis of lysobactin derivatives.

These lysobactin derivatives are derivatives in which one or more amino acids in the ring system of lysobactin are replaced.

The invention further relates to a method for preparing open-chain lysobactin derivatives, in which lysobactin fragment 4-11 is reacted with a tripeptide having a C-terminal aromatic or hydrophobic amino acid in a buffer medium with addition of a $C_{1-4}$-alcohol, whereby the tripeptide is present in the form of the free acid or an ester and whereby the concentration of the $C_{1-4}$-alcohol in the reaction medium is greater than 40%.

The $C_1$-$C_4$ alcohol is, for example, methanol, ethanol or isopropanol, preference is given to methanol.

Preference is given to a method for the enzymatic synthesis of open-chain lysobactin derivatives from lysobactin fragment 4-11 and the tripeptide H-D-X—Y-Phe-OR or H-D-X—Y-(3-cyclohexyl)Ala-OR in a buffer medium with addition of methanol, whereby the methanol concentration in the reaction medium is greater than 40%, R represents hydrogen or C1-C4-alkyl, preferably ethyl or methyl, particularly preferably methyl, D-X represents a natural or synthetic (-amino acid in the D configuration and Y represents a natural or synthetic (-amino acid in the L configuration.

Particular preference is given to a method for the enzymatic synthesis of open-chain lysobactin derivatives from lysobactin fragment 4-11 and the tripeptide H-D-Leu-Leu-Phe-OMethyl, H-D-Leu-Leu-Phe-OH, H-D-Leu-Leu-(3-cyclohexyl)Ala-OMethyl or H-D-Leu-Leu-(3-cyclohexyl)Ala-OH, whereby chymotrypsin is used as enzyme in a buffer medium with addition of methanol, whereby the methanol concentration in the reaction medium is greater than 40%.

DEFINITIONS

Dihydrolysobactin: D-Leu-Leu-Phe-Leu(OH)-Leu-D-Arg-Ile-allo-Thr-Gly-Asn(OH)-Ser

Octahydrolysobactin: D-Leu-Leu-Ala(3-cyclohexyl)-Leu(OH)-Leu-D-Arg-Ile-allo-Thr-Gly-Asn(OH)-Ser Lysobactin fragment 4-11: Leu(OH)-Leu-D-Arg-Ile-allo-Thr-Gly-Asn(OH)-Ser Lysobactin fragment 1-3: D-Leu-Leu-Phe or D-Leu-Leu-Ala(3-cyclohexyl)

The methods used in the course of the chemical and enzymatic reactions and analytical characterizations are listed hereinafter.

DETAILED DESCRIPTION OF PREFERRED EMBODIMENTS

Examples

Abbreviations aq. aqueous
atm Atmosphere (pressure unit)
conc. concentrated
CZE Capillary zone electrophoresis
DCI Direct chemical ionization (in MS)
DCM Dichloromethane
DMSO Dimethyl sulfoxide
EDTA Ethylenediaminetetraacetic acid
EI Electron impact ionization (in MS)
ESI Electrospray ionization (in MS)
h hour(s)
HPLC High pressure, high performance liquid chromatography
HR High resolution
LC-MS Liquid chromatography-coupled mass spectroscopy
LL(3-Cyclohexyl)A D-Leu-Leu-(3-Cyclohexyl)Ala
LLF D-Leu-Leu-Phe
min Minute/minutes
MS Mass spectroscopy
neg. negative
NMR Nuclear magnetic resonance spectroscopy
Pd Palladium
Pd—C Palladium on carbon
pos. positive
PTFE Polytetrafluoroethylene
quant. quantitative
RP-HPLC Reversed-phase HPLC
RT Room temperature
Rt Retention time (in HPLC)
TFA Trifluoroacetic acid
TOF Time of flight
UV Ultraviolet
Vis visible

REFERENCES

For the nomenclature of peptides and cyclodepsipeptides c.f.:

1. A Guide to IUPAC Nomenclature of Organic Compounds (Recommendations 1993), 1993, Blackwell Scientific publications.
2. Nomenclature and symbolism for amino acids and peptides. Recommendations 1983. IUPAC-IUB Joint Commission on Biochemical Nomenclature, UK. *Biochemical Journal* (1984), 219:345-373, as well as cited literature.

General Methods, LC-MS, DR-MS and HPLC

Method 1 (LC-MS): instrument type MS: Micromass ZQ; instrument type HPLC: HP 1100 series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow: 0.0 min 1 ml/min, 2.5 min/3.0 min/4.5 min 2 ml/min; oven: 50° C.; UV detection: 210 nm.

Method 2 (preparative HPLC; symmetry; trifluoroacetic acid): instrument: Gilson Abimed HPLC; UV detector 210 nm; binary pump system; column: SymmetryPrep™$C_{18}$, Waters, 7 μm; 300×19 mm; eluent A: 0.05% trifluoroacetic acid in water, eluent B: 0.05% trifluoroacetic acid in acetonitrile; gradient: 0-5 min 5% B at flow rate 20 ml/min, 5-30 min gradient ramp from 5 to 60% B with the following increases in flow rate: 22 ml/min from 6 min, 23 ml/min from 10 min, 24 ml/min from 15 min; 30-35 min gradient ramp from 60% to 98% B with flow rate reduction to 21 ml/min from 38 min; 40-45 min 10% B.

Method 3 (Method for preparative separation of dihydro- and octahydrolysobactin by HPLC): column: SymmetryPrep™$C_{18}$, Waters, 7 μm 300×19 mm; flow 25 ml/min; RT; eluent A: 0.2% TFA in water, eluent B: acetonitrile, 0-10 min gradient: 80% A, 20% B to 35% A, 65% B; 10.01-15 min: 80% A, 20% B; detection 210 nm. Fractions monitored by means of LC-MS (Method 1), freed from acetonitrile on a rotary evaporator and lyophilized.

Method 4 (analytical HPLC 1100, ZQ2, Phenomenex, Synergi, Hydro-RP): instrument type HPLC: HP 1100 Series; UV DAD; column: Phenomenex, MercuryMS, Synergi 2μ Hydro-RP 20×4 mm; eluent A: water/0.05% formic acid, eluent B: acetonitrile; gradient: 0.0-2.5 min, 90-30% A, flow 1-2 ml/min, 2.5-3.0 min, 30-5% A, flow 2.0 ml/min, 3.0-4.5 min, 5% A; oven: 50° C.; UV detection: 210 nm.

Method 5 (TOF-HR-MS): TOF-HR-MS-ESI+ spectra are recorded using a Micromass LCT instrument (capillary voltage: 3.2 kV, cone voltage: 42 V, source temperature: 120° C., desolvation temperature: 280° C.). For this a syringe pump (Harvard Apparatus) was used for the sample introduction. Leucine enkephalin (Tyr-Gly-Gly-Phe-Leu) is used as standard.

Method 6 (HPLC): instrument type HPLC: HP 1100 Series; UV DAD column: Zorbax Eclipse XBD-C8 (Agilent), 150 mm×4.6 mm, 5 μm; eluent A: 5 ml of $HClO_4$/l of water, eluent B: acetonitrile; gradient: 0-1 min 10% B, 1-4 min 10-90% B, 4-5 min 90% B; flow: 2.0 ml/min; oven: 30° C.; UV detection: 210 and 254 nm.

Method 7 (HPLC): column: Kromasil RP-18, 60 mm×2 mm, 3.5 μm; eluent A: 5 ml of $HClO_4$/l of water, eluent B: acetonitrile; gradient: 0 min 2% B, 0.5 min 2% B, 4.5 min 90% B, 9 min 90% B; flow: 0.75 ml/min; oven: 30° C.; UV detection: 210 nm.

Method 8 (HPLC): column: Kromasil RP-18, 250 mm×4 mm, 5 μm; eluent A: 5 ml of $HClO_4$/l of water, eluent B: acetonitrile; gradient: 0 min 5% B, 10 min 95% B; flow: 1 ml/min; oven: 40° C.; UV detection: 210 nm.

Method 9 (HPLC): column: Kromasil RP-18, 250 mm×4 mm, 5 μm; eluent A: 2 ml of $HClO_4$/l of water, eluent B: acetonitrile; isocratic: 45% B, 55% A; flow: 1 ml/min; oven: 40° C.; UV detection: 210 nm.

Method 10 (HPLC): instrument: Agilent 1100 with DAD (G1315B), binary pump (G1312A), autosampler (G1313A), solvent degasser (G1379A) and column thermostat (G1316A); column: Agilent Eclipse XDB-C8 4.6×150×5 mm; column temperature: 40° C.; eluent A: 0.05% of 70% perchloric acid in water; eluent B: methanol; flow: 2.00 ml/min; isocratic: 0-7 min 55% B.

Method 11 (HPLC): analytical HPLC method bromelain/chymotrypsin cleavage. About 20 μg of the enzymatic cleavage products or of the starting compounds are chromatographed on a 300SB-C18 column (4.6 mm×125 mm; 3.5 μm material; 300 Angström pore diameter). As eluent, an acetonitrile/TFA gradient is used. Eluent A: 0.1% TFA in water, eluent B: 0.1% TFA in 60% acetonitrile/40% water; gradient: 0 min 0% B, 2 min 10% B, 50 min 80% B, 52 min 100% B, 55 min 0% B, 60 min 0% B; flow: 0.7 ml/min; column temperature: 40° C.; detection: 210 nm.

Proteinchemical Characterization of Dihydro-, Ocatahydrolysobactin and the Enzymatic Cleavage Products Instruments The sequence analyses are carried out using a protein sequencer Procise™ from Applied Biosystems. The standard sequencing program is used. The sequencer, the various sequencing programs as well as the PTH detection system are described in detail in the operating handbook User's Manual Set, Protein Sequencing System Procise™ (1994), Applied Biosystems Forster City, Calif. 94404, U.S.A.

The reagents for operating the sequencer and the HPLC column for the PTH detection are obtained from Applied Biosystems.

The HPLC analyses are carried out using an HP1100 HPLC system from Agilent. A Zorbax 300SB-C18 column (4.6 mm×150 mm; 3.5 μm material; 300 Angström pore diameter) from Agilent (D-Waldbronn) is used for the separations.

The reagents used are of HPLC quality and are obtained from Merck (D-Darmstadt).

The capillary electrophoresis model 270A-HT is from Applied Biosystems. The samples are generally injected hydrodynamically over various time periods. The capillary column used (50 μm diameter×72 cm in length) is from Applied Biosystems. Separation programs and the function of the analyzer are described extensively in the handbook of the instrument (User's manual capillary electrophoresis system model 270A HT; Applied Biosystems Forster City, Calif. 94404, U.S.A.; 1989).

The reagents used are of biochemical quality and are obtained from Merck (D-Darm-stadt) or Sigma (D-Deisenhofen).

The amino acid analyses are carried out using an LC3000 amino acid analyzer from Eppendorf/Biotronik. A slightly modified standard separation program from Eppendorf/Biotronik is used. The separation programs and the function of the analyzer are extensively described in the instrument handbook (Handbuch des Aminosäureanalysators LC 3000 [handbook of the LC 3000 amino acid analyzer], Wissenschaftliche Geräte GmbH Biotronik, Maintal, 1996).

The reagents used are of biochemical quality and are obtained from Merck (D-Darmstadt), Fluka (D-Neu-Ulm) or Sigma (D-Deisenhofen).

The molecular weights are determined using a ZQ-1 system from Micromass (Manchester, UK). The fragments are thereby separated by means of RP-18-HPLC chromatography (HP1100 system) and the molecular weight is determined by electron spray ionization (ESI). External calibration is carried out. The calibration and functioning of the systems are extensively described in the handbook of the instrument.

The enzymes and chemicals used are of biochemical quality and are obtained from Fluka, Calbiochem (D-Heidelberg) and Sigma.

The material for the preparative chromatography source 15RPC is obtained from Amersham Bioscience (D-Freiburg). The preparative separation is carried out using an ÄKTA™ system from Amersham Bioscience.

The chemical compounds mentioned in the invention can also be in the form of salts, solvates or solvates of the salts.

Salts preferred for purpose of the present invention are physiologically acceptable salts of the compounds which can be prepared or are useable according to the invention. However, also comprised are salts which are not themselves suitable for pharmaceutical applications, but can be used, for example, for the isolation or purification of the compounds which can be prepared or are useable according to the invention, or mixed salts.

Physiologically acceptable salts of the compounds which can be prepared or are useable according to the invention comprise acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds which can be prepared or are useable according to the invention also comprise salts of usual bases such as, for example, and preferably, alkali metal salts (for example sodium and potassium salts), alkaline earth metal salts (for example calcium and magnesium salts) and ammonium salts, derived from ammonia or organic amines having 1 to 16 carbon atoms, such as, for example, and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates, for the purpose of the invention refer to those forms of the compounds which can be produced or are useable according to the invention which, which in solid or liquid state, form a complex by coordination with solvent molecules. Hydrates are a special form of solvates in which the coordination takes place with water.

Example 1

D-Leucyl-N-1-{(3S,6S,12S,15S,18R,21S,24S,27S, 28R)-6-[(1S)-2-amino-1-hydroxy-2-oxoethyl-]18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide Bistrifluoroacetate D-Leucyl-L-leucyl-[(3R)-3-hydroxy-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine-C1$^{0.11}$-O3$^{0.3}$-lactone bistrifluoroacetate} (Lysobactin)

Fermentation:
Culture Medium:

YM: yeast-malt agar: D-glucose (4g/l), yeast extract (4g/l), malt extract (10g/l), 1 liter of Lewatit water. Before sterilization (20 minutes at 121° C.), the pH is adjusted to 7.2.

HPM: mannitol (5.4 g/l), yeast extract (5 g/l), meat peptone (3g/l).

Working preserve: The lyophilized strain (ATCC 53042) is grown in 50 ml of YM medium.

Flask fermentation: 150 ml of YM medium or 100 ml of HPM medium in a 1 l Erlenmeyer flask are inoculated with 2 ml of the working preserve and allowed to grow on a shaker at 240 rpm for 30-48 hours at 28° C.

30 l fermentation: 300 ml of the flask fermentation (HPM medium) are used to inoculate a sterile 30 l nutrient medium solution (1 ml of antifoam SAG 5693/1). This culture is allowed to grow for 21 hours at 28° C., 300 rpm and aeration with sterile air of 0.3 vvm. The pH is kept constant at Ph=7.2 with 1 M hydrochloric acid. In total, 880 ml of 1 M hydrochloric acid are added during the culturing period.

Main culture (200 l): 15×150 ml of YM medium in 1 l Erlenmeyer flasks are inoculated with 2 ml of the working preserve and allowed to grow on the shaker at 28° C. for 48 hours and at 240 rpm. 2250 ml of this culture are used to inoculate a sterile 200 l nutrient media solution (YM) (1 ml of antifoam SAG 5693/1) and it is allowed to grow for 18.5 hours at 28° C., 150 rpm and aeration with sterile air of 0.3 vvm.

Hourly samples (50 ml) are taken to check the course of the fermentation. 1 ml of methanol (0.5% trifluoroacetic acid) is added to 2 ml of this culture broth and the mixture is filtered through a 0.45 μm filter. 30 μl of this suspension are analyzed means of by HPLC (Method 6 and Method 7).

After 18.5 hours, the culture broth of the main culture is separated into supernatant and sediment at 17 000 rpm.

Isolation:

The supernatant(183 l) is adjusted to pH 6.5 (7 using concentrated trifluoroacetic acid or a sodium hydroxide solution and loaded onto a Lewapol column (OC 1064, 60 l contents). Elution is subsequently carried out with pure water, water/methanol 1:1 and subsequently with pure methanol (containing 0.1% trifluoroacetic acid). This organic phase is concentrated in vacuo to a residual aqueous residue of 11.5 l.

The residual aqueous phase is bound to silica gel $C_{18}$ and separated (MPLC, Biotage Flash 75, 75×30 cm, KP-C18-WP, 15-20 μm, flow: 30 ml; eluent: acetonitrile/water containing 0.1% trifluoroacetic acid; gradient: 10%, 15% and 40% acetonitrile). The 40% acetonitrile phase which contains the main amount of Example 1A, is concentrated in vacuo and subsequently lyophilized (about 13g). This mixture of solids is separated in 1.2 g portions, first on a preparative HPLC (Method 1), subsequently by gel filtration on Sephadex LH-20 (5×70 cm, acetonitrile/water 1:1, in each case containing 0.05% trifluoroacetic acid) and a further preparative HPLC (Method 8).

This process yields 2250 mg of Example 1.

The sediment is taken up in 4 l of acetone/water 4:1, 2 kg of Celite are added, the mixture is adjusted to pH=6 using trifluoroacetic acid, stirred and centrifuged. The solvent is concentrated in vacuo and the residue is freeze dried. The lyophilizate obtained (89.9 g) is taken up in methanol, filtered, concentrated and separated on silica gel (Method 9). Example 1A is then purified by gel filtration (Sephadex LH-20, 5×68 cm, water/acetonitrile 9:1 (containing 0.05% trifluoroacetic acid), flow: 2.7 ml/min, fraction size 13.5 ml) to give the pure substance.

$^1$H NMR (500.13 MHz, $d_6$-DMSO): δ=0.75 (d, 3H), 0.78 (d, 6H), 0.80 (t, 3H), 0.82 (d, 3H), 0.90 (d, 3H), 0.91 (d, 3H), 0.92 (d, 3H), 0.95 (d, 3H), 0.96 (d, 3H), 1.05 (m, 1H), 1.19 (d,

3H), 1.25 (m, 2H), 1.50 (m, 4H), 1.51 (m, 2H), 1.55 (m, 1H), 1.61 (m, 1H), 1.65 (m, 1H), 1.84 (m, 1H), 1.85 (m, 11H), 1.86 (m, 1H), 1.89 (m, 1H), 1.95 (m, 1H), 2.75 (m, 2H), 3.40 (m, 1H), 3.52 (m, 2H), 3.53 (dd, 1H), 3.64 (m, 2H), 3.66 (m, 1H), 3.68 (dd, 1H), 3.73 (m, 2H), 4.00 (dd, 1H), 4.02 (br., 1H), 4.13 (br., 1H), 4.32 (dd, 1H), 4.39 (t, 1H), 4.55 (m, 1H), 4.75 (dd, 1H), 5.19 (t, 1H), 5.29 (d, 1H), 5.30 (br., 1H), 5.58 (m, 2H), 6.68 (m, 3H), 6.89 (d, 1H), 6.93 (m, 3H), 6.94 (br., 1H), 6.98 (d, 1H), 7.12 (br., 1H), 7.20 (br., 2H), 7.23 (m, 2H), 7.42 (m, 2H), 7.54 (d, 1H), 7.58 (d, 1H), 8.32 (br., 1H), 9.18 (br., 1H), 9.20 (m, 2H), 9.50 (br., 1H).

$^{13}$C-NMR (125.77 MHz, d$_6$-DMSO): δ=10.3, 15.3, 19.0, 19.2, 19.6, 20.0, 20.9, 22.0, 22.4, 23.0, 23.2, 24.3, 24.4, 25.0, 25.4, 26.0, 27.8, 30.9, 35.4, 39.5, 40.8, 40.9, 41.6, 44.1, 51.5, 52.7, 55.9, 56.2, 56.4, 57.9, 58.8, 60.2, 61.1, 62.6, 70.1, 71.6, 71.7, 75.5, 128.1, 128.6, 136.7, 156.8, 168.2, 170.1, 170.4, 171.2, 171.5, 171.9, 172.2, 172.4, 173.7.

The assignment of the signals was carried out according to the assignment described in the literature (T. Kato, H. Hinoo, Y. Terui, J. Antibiot. (1988) 61:719-725).

Example 2 and Example 3

D-Leu-Leu-Phe-[(3R)-Leu(3-OH)]-Leu-D-Arg-Ile-aThr-Gly-[(3S)-3-Asn(3-OH)]-Ser-trifluor-oacetate (Dihydrolysobactin) and D-Leu-Leu-Ala(3-cyclohexyl)-[(3R)-Leu(3-OH)]-Leu-D-Arg-Ile-aThr-Gly-[(3S)-3-Asn(3-OH)]-Ser-trifluoroacetate (Octahydrolysobactin)

Hydrogenation Method 1:

The compound from Example 1 (lysobactin, 250 mg, 170 μmol) is dissolved in isopropanol/water (2:1, 60 ml) andhydrogenated under 1 atm of hydrogen in the presence of 200 mg of Pd (10% on carbon). The course of the reaction is followed by means of LC-MS (Method 1). After virtually complete conversion (>95%), the catalyst is filtered off, washed with isopropanol and the filtrate is lyophilized. In this crude product, according to LC-MS, the products are distributed as follows: dihydrolysobactin about 74%, octahydrolysobactin about 12%. The residue is purified by HPLC (Method 2). After lyophilization of the suitable fractions, the pure compound Example 2 is obtained (81.5 mg, 31% of theory).

LC-MS: (Method 1): R$_f$=1.56 min ES$^+$: m/z=1279 [M+H]$^+$, 640.1 [M+2H]$^{2+}$; ES$^-$: m/z=1277 [M−H]$^-$, 638.1 [M−2H]$^{2-}$.

See Table 1 for the peptide sequences of the hydrolysobactins.

Hydrogenation Method 2:

By hydrogenation under a hydrogen pressure of 3 atm, in a method otherwise identical to hydrogenation method 1, the following distribution in the crude product determined by LC-MS is obtained: dihydrolysobactin about 80%, octahydrolysobactin about 17%. After HPLC purification (Method 2), the pure compound Example 2 is obtained (86 mg, 33% of theory).

Hydrogenation Method 3:

With a prolonged hydrogenation period at 3 bar hydrogen or using a higher pressure (up to 80 bar hydrogen pressure), proportionately more octahydrolysobactin can be obtained.

Dihydrolysobaction

Octahydrolysobaction

In most cases, the crude mixtures of dihydro- and octahydrolysobactin are not separated, but are used directly in the enzymatic cleavage.

Hydrogenation Method 4:

In the following case the compound octahydrolysobactin is also isolated in pure form:

Lysobactin (Example 1, 1.04 g, 0.69 mmol) is dissolved in isopropanol/water (2:1, 90 ml) and hydrogenated under 3 atm hydrogen for 7 days in the presence of 200 mg of Pd (10% on carbon). The catalyst is filtered off, washed with isopropanol and the filtrate is freed from isopropanol on a rotary evaporator and then lyophilized. In this crude product the products are distributed according to LC-MS (Method 1) as follows: dihydrolysobactin about 65%, octa-hydrolysobactin about 35%. The residue is purified by HPLC (Method 2, subsequently Method 3). Dihydrolysobactin (Example 2) (280 mg, 27% of theory) and octahydrolysobactin (Example 3) (212 mg, 20% of theory) are obtained.

LC-MS: (Method 1): $R_t$=1.63 min ESIpos.: m/z=643.3 (100) $[M+2H]^{2+}$; ESIneg.: m/z=1283 $[M-H]^-$, 641.2 $[M-2H]^{2-}$.

Hydrogenation Method 5:

As an example of a hydrogenation under high pressure hydrogen, after 4 days at 40° C. and 50 bar hydrogen, the following crude mixture is obtained according to LC-MS (Method 1): 45% dihydrolysobactin and 45% octahydrolysobactin.

Hydrogenation Method 6:

Lysobactin bistrifluoroacetate (Example 1, 500 mg, 0.33 mmol) is dissolved in isopropanol/water 2:1 (30 ml). Under an argon protective gas atmosphere, 10 percent palladium on carbon (100 mg) is added. The reaction mixture is stirred (after degassing) in a pressure autoclave at 80-70 bar hydrogen and RT for 48 h. 10% palladium on carbon (100 mg) is again added to the reaction. The reaction mixture is (after degassing) again stirred in a pressure autoclave at 80-70 bar hydrogen and RT for 48 h. Now no lysobactin is detectable any more by means of HPLC (for example Method 4). The reaction mixture is filtered through a glass frit (pore size 2 or 3), concentrated in vacuo, again taken up in methanol/0.2% glacial acetic acid, filtered through a syringe filter (Biotage, PTFE), concentrated in vacuo and dried under high vacuum. 496 mg (quant.) of product (80% dihydrolysobactin, 20% octahydrolysobactin) are obtained.

Hydrogenation Method 7:

Lysobactin monotrifluoroacetate monoacetate (5 mg, 3.45 µmol) is hydrogenated in a mixture of isopropanol (2 ml), water (0.25 ml) and acetic acid (0.05 ml) in the presence of platinum dioxide (20 mg) at 80 bar and 50° C. After 17 h, the pressure is relieved, the system is vented with argon and the suspension freed from the catalyst by means of a microfilter. LC-MS analysis of the filtrate (Method 4) shows 7% of theory octahydrolysobactin ($R_t$=1.54 min, Method 4).

Hydrogenation Method 8:

Lysobactin bistrifluoroacetate (Example 1A, 10g, 6.65 mmol) is dissolved in isopropanol/water 9:2 (110 ml). Under an argon protective gas atmosphere, palladium on carbon (10%; 5g) is added. The reaction mixture (after degassing) is stirred in a pressure autoclave at 80-70 bar hydrogen pressure and 40° C. for 12 h. Palladium on carbon (10%; 5g) is again added to the reaction. The reaction mixture (after degassing) is again stirred in a pressure autoclave at 80-70 bar hydrogen pressure and 40° C. for 12 h. The reaction mixture (after degassing) is once again stirred in a pressure autoclave at 80-70 bar hydrogen pressure and 40° C. for 12 h. Now no lysobactin is detectable any more by means of analytical HPLC (Method 10). The reaction mixture is filtered through kieselguhr, concentrated in vacuo and dried under a high vacuum. 9.17 g (99% of theory) of product (60% dihydrolysobactin, 40% octahydrolysobactin) are obtained.

Hydrogenation Method 9:

Lysobactin bistrifluoroacetate (Example 1A, 5g, 3.32 mmol) is dissolved in isopropanol/water 9:2 (110 ml). Under an argon protective gas atmosphere, palladium on carbon (10%; 5g) is added. The reaction mixture (after degassing) is stirred in a pressure autoclave at 80 bar hydrogen pressure and 40° C. for 12 h. The reaction mixture is filtered through kieselguhr, concentrated in vacuo and dried under high vacuum. The hydrogenation is repeated a further three times each time using 5.0 g of lysobactin bistrifluoroacetate (in total: 4 passes). As combined product fraction 18.27 g of product (dihydro-lysobactin:octahydrolysobactin, about 5:4) are obtained.

Example 4

Chymotrypsin Cleavage of Dihydrolysobactin, Enzyme/Substrate Ratio 1:50

200 µg of dihydrolysobactin are dissolved in 10 µl of methanol and then 190 µl of cleavage buffer (0.1 M ammonium hydrogencarbonate/0.5 M urea pH 8) are added. 4 µg of chymotrypsin (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis by HPLC, capillary zone electrophoresis, sequence analysis, amino acid analysis, or MS study.

See Table 2 the for the peptide sequences of the chymotrypsin cleavage products.

Example 5

Chymotrypsin Cleavage of Octahydrolysobactin, Enzyme/Substrate Ratio 1:50

200 µg of octahydrolysobactin are dissolved in 10 µl of methanol and then 190 µl of cleavage buffer (0.1 M ammonium hydrogencarbonate/0.5 M urea pH 8) are added. 4 µg of chymotrypsin (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 2 for the peptide sequences of the chymotrypsin cleavage products.

Example 6

Analytical Chymotrypsin Cleavage of the Mixture Dihydro-/Octahydrolysobactin, Enzyme Substrate Ratio 1:25

200 µg of dihydro- (59%) and octahydrolysobactin (34%) are dissolved in 10 µl of methanol and then 190 µl of cleavage buffer (0.1 M ammonium hydrogencarbonate/0.5 M urea pH 8) are added. 8 µg of chymotrypsin (1:25) are added and the reaction is carried out at 37° C. Aliquots of 30 µl are taken after 0, 0.5, 1, 3 h and the enzyme cleavage is stopped with 30 µl of acetonitrile/1% TFA. The samples are stored at −20° C. until analysis.

See Table 2 for the peptide sequences of the chymotrypsin cleavage products.

Example 7

Analytical Chymotrypsin Cleavage of the Mixture Dihydro-/Octahydrolysobactin, Enzyme Substrate Ratio 1:400

150 µg of dihydro- (59%) and octahydrolysobactin (34%) are dissolved in 15 µl of ethanol and then 126 µl of cleavage buffer (0.1 M ammonium hydrogencarbonate/0.5 M urea pH 8) are added. 0.38 µg of chymotrypsin (9 µl of chymotrypsin solution water/ethylene glycol/cleavage buffer, 0.2 mg/ml; 1:400) are added and the reaction is carried out at 37° C. Aliquots of 25 µl are taken after 0, 0.5, 1, 3 h and the enzyme cleavage is stopped with 25 µl of 30% acetonitrile/0.1% TFA. The samples are stored at −20° C. until analysis.

See Table 2 for the peptide sequences of the chymotrypsin cleavage products.

Example 8

Analytical Chymotrypsin Cleavage of the Mixture Dihydro-/Octahydrolysobactin Substrate Concentration 6 mg/ml 900 µg of dihydro- (59%) and octahydrolysobactin (34%) are dissolved in 15 µl of methanol and then 99 µl of cleavage buffer (0.1 M ammonium hydrogencarbonate/0.5 M urea pH 8) are added. 36 µg of chymotrypsin (36 µl of chymotrypsin solution water/ethylene glycol 1:1, 1 mg/ml; 1:25) are added and the reaction is carried out at 37° C. Aliquots of 25 µl are taken after 0, 0.5, 1, 3 h and the enzyme cleavage is stopped with 25 µl of 30% acetonitrile/0.1% TFA. The samples are stored at −20° C. until analysis.

See Table 2 for the peptide sequences of the chymotrypsin cleavage products.

Example 9

Analytical Chymotrypsin Cleavage of the Mixture Dihydro-/Octahydrolysobactin Solvent Concentration 30% Methanol 150 µg of dihydro- (59%) and octahydrolysobactin (34%) are dissolved in 45 µl of methanol and then 99 µl of cleavage buffer (0.1 M ammonium hydrogencarbonate/0.5 M urea pH 8) are added. 6 µg of chymotrypsin (6 µl of chymotrypsin solution water/ethylene glycol 1:1, 1 mg/ml; 1:25) are added and the reaction is carried out at 37° C. Aliquots of 25 µl are taken after 0, 0.5, 1, 3 h and the enzyme cleavage is stopped with 25 µl of 30% acetonitrile/0.1% TFA. The samples are stored at −20° C. until analysis.

See Table 2 for the peptide sequences of the chymotrypsin cleavage products.

Example 10

Analytical Chymotrypsin Cleavage of the Mixture Dihydro-/Octahydrolysobactin Cleavage at Room Temperature

200 µg of dihydro- (59%) and octahydrolysobactin (34%) are dissolved in 10 µl of methanol and then 190 µl of cleavage buffer (0.1 M ammonium hydrogencarbonate/0.5 M urea pH 8) are added. 8 µg of chymotrypsin (8 µl of chymotrypsin solution water/ethylene glycol 1:1, 1 mg/ml; 1:25) are added and the reaction is carried out at room temperature (20-25° C.). Aliquots of 30 µl are taken after 0, 0.5, 1, 3, 6 h and the enzyme cleavage is stopped with 30 µl of 30% acetonitrile/1% TFA. The samples are stored at −20° C. until analysis.

See Table 2 for the peptide sequences of the chymotrypsin cleavage products.

Example 11

Fragment 4-11

[(3R)-Leu(3-OH)]-Leu-D-Arg-Ile-aThr-Gly-[(3S)-3-Asn(3-OH)]-Ser Trifluoroacetate

Preparative Chymotrypsin Cleavage of Dihydrolysobactin Substrate Concentration 1 mg/ml 2×80 mg of dihydrolysobactin (35.3 µmol and 33.8 µmol of pure peptide determined by amino acid analysis) are dissolved in 8 ml of methanol each and then 69 ml of cleavage buffer (0.1 M ammonium hydrogencarbonate/0.5 M urea pH 8) each are added. Before the addition of enzyme, the solutions are warmed to 37° C. in a drying cabinet. 3.2 mg of chymotrypsin (3.2 ml of chymotrypsin solution water/ethylene glycol 1:1, 1 mg/ml; 1:25; preheated to 37° C.) are added and the reactions are carried out at 37° C. Aliquots of 200 µl are taken after 0.5, 1 h and the enzyme cleavages are stopped with 200 µl of 30% acetonitrile/0.1% TFA. The samples are analyzed by HPLC in parallel to the enzyme cleavages within 15 min (retention time fragment 4-11 about 3.6 min, fragment 1-3 (LLF) about 9.6 min, conditions: solvent A 0.1% TFA, solvent B 60% acetonitrile/0.1% TFA, gradient: 0 min 30% B, 10 min 80% B, 11 min 100% B, 12 min 30% B, 15 min 30% B; flow 0.7 ml/min, 40° C., UV detection 210 nm). The enzyme reactions are stopped after about 70 min with 3 ml of acetonitrile and about 0.6 ml of TFA. The pH of the solution is between 1 and 2. The solutions can be stored at −20° C. until the preparative separation.

Preparative Separation of Fragments 1-3 and 4-11

2× about 80 ml of the cleavage solutions are filtered through a filter (0.2 μm) and then combined. The solution is divided into four portions each of about 38.5 ml (total 154 ml) and each is chromatographed on a Source 15RPC column (3 ml) using an acetonitrile/TFA gradient. Conditions: solvent A 0.1% TFA, solvent B 0.1% TFA/acetonitrile; gradient: 0% B to 45% B in 40 min; flow 2 ml/ min; UV detection 210 nm. The four runs are carried out sequentially and the fractions are collected in the same tube. The resultant chromatograms are identical.

Fragments 4-11 (Rt=about 15 min) and 1-3 (LLF) (Rt=about 25 min) are combined, diluted 1:1 with water and then lyophilized.

200 μl aliquots of the respective pools are lyophilized separately for amino acid analysis, analytical HPLC, capillary zone electrophoresis (CZE), sequence analysis and mass spectrometry.

The yield of fragment 4-11 according to amino acid analysis is 68.3 μmol (99% of theory) and of fragment 1-3 67.4 μmol (98% of theory).

Example 12

Preparative Chymotrypsin Cleavage of the Mixture Dihydro/Octahydrolysobactin 1 mg/ml Batch 1

2×700 mg of dihydro- (56%) and octahydrolysobactin (21%) (682 μmol of dihydro- and octahydrolysobactin present as pure peptides determined by amino acid analysis) are dissolved in 70 ml of methanol each and then 602 ml of cleavage buffer (0.1 M ammonium hydrogencarbonate/0.5 M urea pH 8) each are added. Before the addition of enzyme the solutions are warmed to 37° C. in a drying cabinet. 28 mg of chymotrypsin (28 ml of chymotrypsin solution water/ethylene glycol 1:1, 1 mg/ml; 1:25; 37° C. preheated) are added and the reactions are carried out at 37° C. Aliquots of 200 μl are taken after 0.5, 1 h and the enzyme cleavages are stopped with 200 μl of 30% acetonitrile/0.1% TFA. The samples are analyzed by HPLC in parallel to the enzyme cleavages within 15 min (retention time fragment 4-11 about 3.6 min, fragment 1-3 (LLF) about 9.6 min, fragment 1-3 (LL(3-cyclohexyl)A) about 11.3 min, conditions: solvent A 0.1% TFA, solvent B 60% acetonitrile/0.1% TFA, gradient: 0 min 30% B, 10 min 80% B, 11 min 100% B, 12 min 30% B, 15 min 30% B; flow 0.7 ml/min, 40° C., UV detection 210 nm). The enzyme reactions are stopped after about 60 min with 30 ml of acetonitrile and about 6 ml of TFA. The pH of the solution is between 1 and 2. The solutions can be stored at −20° C. until the preparative separation.

Batch 2

775 mg of dihydro- (45%) and octahydrolysobactin (48%) (468 μmol of dihydro- and octahydrolysobactin present as pure peptides determined by amino acid analysis) are dissolved in 77.5 ml of methanol and then 667 ml of cleavage buffer (0.1M ammonium hydrogencarbonate/0.5M urea pH 8) are added. Before the addition of the enzyme the solution is warmed to 37° C. in a drying cabinet. 31 mg of chymotrypsin (31 ml of chymotrypsin solution water/ethylene glycol 1:1, 1 mg/ml; 1:25; 37° C. preheated) are added and the reaction is carried out at 37° C. Aliquots of 200 μl are taken after 0.5, 1 h and the enzyme cleavage is stopped with 200 μl of 30% acetonitrile/0.1% TFA. The samples are analyzed by HPLC in parallel to the enzyme cleavage within 15 min (retention time fragment 4-11 about 3.6 min, fragment 1-3 (LLF) about 9.6 min, fragment 1-3 (LL(3-cyclohexyl)A) about 11.3 min) (solvent A 0.1% TFA, solvent B 60% acetonitrile/0.1% TFA, gradient: 0 min 30% B, 10 min 80% B, 11 min 100% B, 12 min 30% B, 15 min 30% B; flow 0.7 ml/min, temperature: 40° C., UV detection 210 nm). The enzyme reaction is stopped after 60 min with 30 ml of acetonitrile and about 6 ml of TFA. The pH of the solution should be between 1 and 2. The solution can be stored at −20° C. until the preparative separation.

Preparative Separation of Fragments 1-3 and 4-11

The cleavage batches 1 and 2 are filtered through a filter (0.2 μm) and then combined. The solution is divided into several portions and each is chromatographed on a Source 15RPC column using an acetonitrile/TFA gradient as described above. The runs are carried out successively and the fractions collected in the same tube. The resultant chromatograms are identical.

Fragment 4-11 (Rt. about 15 min) is combined, diluted 1:1 with water and then lyophilized.

The yield of fragment 4-11, after lyophilization, is 1.1 g (1095 μmol). For a starting amount of 1150 μmol of cleavable material, the yield of fragment 4-11 is 95% of theory.

Example 13

Preparative Chymotrypsin Cleavage of the Mixture Dihydro/Octahydrolysobactin Substrate Concentration 3 mg/ml 2×0.995 g of a mixture of dihydro- (52%) and octahydrolysobactin (37%) are dissolved in 33 ml of methanol each and then 257 ml of cleavage buffer (0.1M ammonium hydrogencarbonate/0.5 M urea pH 8) each are added. Before the addition of the enzyme the solution is warmed to 37° C. in a drying cabinet. 39.6 mg of chymotrypsin (39.6 ml of chymotrypsin solution water/ethylene glycol 1:1, 1 mg/ml; 1:25; 37° C. preheated) are added and the reaction is carried out at 37° C. Aliquots of 200 μl are taken after 0.5, 1 h and the enzyme cleavage is stopped with 200 μl of 30% acetonitrile/0.1% TFA. The samples are analyzed by HPLC in parallel to the enzyme cleavage within 15 min (retention time fragment 4-11 about 3.6 min, fragment 1-3 (LLF) about 9.6 min, fragment 1-3 (LL(3-cyclohexyl)A) about 11.3 min) (solvent A 0.1% TFA, solvent B 60% acetonitrile/0.1% TFA, gradient: 0 min 30% B, 10 min 80% B, 11 min 100% B, 12 min 30% B, 15 min 30% B; flow: 0.7 ml/min, temperature: 40° C., UV detection 210 nm). The enzyme reactions are stopped after 60 min with 30 ml of acetonitrile and about 2.5 ml of TFA each. The pH of the solution should be between 1 and 2. The solution can be stored at −20° C. until the preparative separation.

Example 14

Preparative Chymotrypsin Cleavage of the Mixture Dihydro/Octahydrolysobactin Substrate Concentration 5 mg/ml 10g of dihydro- (about 40%) and octahydrolysobactin (about 60%) are dissolved in 200 ml of methanol and then 1700 ml of cleavage buffer (0.1 M ammonium hydrogencarbonate/0.5 M urea pH 8) are added. Before the addition of the enzyme the solution is warmed to 37° C. in a drying cabinet. 400 mg of chymotrypsin (100 ml of chymotrypsin solution water/ethylene glycol 1:1, 4 mg/ml; 1:25; 37° C. preheated) are added and the reaction is carried out at 37° C. Aliquots of 200 µl are taken after 0.5, 1 h and the enzyme cleavage is stopped with 200 µl of 30% acetonitrile/0.1% TFA. The samples are analyzed by HPLC in parallel to the enzyme cleavage within 15 min (retention time fragment 4-11 about 3.6 min, fragment 1-3 (LLF) about 9.6 min, fragment 1-3 (LLA(3-cyclohexyl)) about 11.3 min) (solvent A 0.1% TFA, solvent B 60% acetonitrile/0.1% TFA, gradient 0 min 30% B, 10 min 80% B, 11 min 100% B, 12 min 30% B, 15 min 30% B; flow 0.7 ml/min, temperature: 40° C., UV detection 210 nm). The enzyme reaction is stopped after 60 min with 75 ml of acetonitrile and about 15 ml of TFA. The pH of the solution should be between 1 and 2. The solution can be stored at −20° C. until the preparative separation.

Fragment 4-11 is isolated as described above by preparative HPLC in several runs.

The activity of the chymotrypsin batch used (70 U/mg) is checked by a control cleavage using the protein interleukin-4 double mutein Arg(121)→Asp(121)/Tyr(124)→Asp(124) (BAYER Healthcare AG, D-Wuppertal).

Example 15

Subtilisin Cleavage of Dihydrolysobactin

200 µg of dihydrolysobactin are dissolved in 10 µl of methanol and then 190 µl of cleavage buffer (0.1 M ammonium hydrogencarbonate/0.5 M urea pH 8) are added. 4 µg of subtilisin (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 3 for the peptide sequences of the subtilisin cleavage products.

Example 16

Subtilisin Cleavage of Octahydrolysobactin

200 µg of octahydrolysobactin are dissolved in 10 µl of methanol and then 190 µl of cleavage buffer (0.1 M ammonium hydrogencarbonate/0.5 M urea pH 8) are added. 4 µg of subtilisin (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 3 for the peptide sequences of the subtilisin cleavage products.

The activity of the subtilisin batch used (about 12 U/mg) is checked by a control cleavage using the protein interleukin-4 double mutein Arg(121)→Asp(121)/Tyr(124)→Asp(124) (BAYER Healthcare AG, D-Wuppertal).

Example 17

Thermolysin Cleavage of Dihydrolysobactin

200 µg of dihydrolysobactin are dissolved in 10 µl of methanol and then 190 µl of cleavage buffer (0.1 M tris (hydroxymethyl)aminomethane/5 mM calcium chloride pH 7.45) are added. 4 µg of thermolysin (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 4 for the peptide sequences of the thermolysin cleavage products.

Example 18

Thermolysin Cleavage of Octahydrolysobactin

200 µg of octahydrolysobactin are dissolved in 10 µl of methanol and then 190 µl of cleavage buffer (0.1 M ammonium hydrogencarbonate/0.5 M urea pH 8) are added. 4 µg of thermolysin (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 4 for the peptide sequences of the thermolysin cleavage products.

The activity of the thermolysin batch used (about 55 U/mg) is checked by a control cleavage using the protein interleukin-4 double mutein Arg(121)→Asp(121)/Tyr(124)→Asp(124) (BAYER Healthcare AG, D-Wuppertal).

Example 19

Papain Cleavage of Dihydrolysobactin

200 µg of dihydrolysobactin are dissolved in 10 µl of methanol and then 190 µl of cleavage buffer (0.1 M sodium phosphate/10 mM cysteine, 2 mM EDTA pH 6.5) are added. 4 µg of papain (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 5 for the peptide sequences of the papain cleavage products.

Example 20

Papain Cleavage of Octahydrolysobactin

200 µg of octahydrolysobactin are dissolved in 10 µl of methanol and then 190 µl of cleavage buffer (0.1 M sodium phosphate/10 mM cysteine, 2 mM EDTA pH 6.5) are added. 4 µg of papain (1:50) are added and the reaction is carried out at 37° C. Aliquots of 30 µl are taken after 0, 0.5, 1, 3, 6 and 24 b and the enzyme cleavage is stopped with 30 µl of acetonitrile/1% TFA. The samples are stored at −20° C. until analysis.

See Table 5 for the peptide sequences of the papain cleavage products.

The activity of the papain batch used (about 11 U/mg) is checked by a control cleavage using the protein interleukin-4 double mutein Arg(121)→Asp(121)/Tyr(124)→Asp(124) (BAYER Healthcare AG, D-Wuppertal).

Example 21

Proteinase K Cleavage of Dihydrolysobactin

200 µg of dihydrolysobactin are dissolved in 10 µl of methanol and then 190 µl of cleavage buffer (0.1 M sodium tetraborate pH 9) are added. 4 µg of proteinase K (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 6 for the peptide sequences of the proteinase K cleavage products.

Example 22

Proteinase K Cleavage of Octahydrolysobactin

200 µg of octahydrolysobactin are dissolved in 10 µl of methanol and then 190 µl of cleavage buffer (0.1 M sodium tetraborate pH 9) are added. 4 µg of proteinase K (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 6 for the peptide sequences of the proteinase K cleavage products.

The activity of the proteinase K batch used (about 30 U/mg) is checked by a control cleavage using the protein interleukin-4 double mutein Arg(121)→Asp(121)/Tyr (124)→Asp(124) (BAYER Healthcare AG, D-Wuppertal).

Example 23

Bromelain Cleavage of Dihydrolysobactin

200 µg of dihydrolysobactin are dissolved in 10 µl of methanol and then 190 µl of cleavage buffer (0.1 M sodium phosphate, 10 mM cysteine, 2 mM EDTA pH 6.5) are added. 4g of bromelain (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 7 for the peptide sequences of the bromelain cleavage products.

Example 24

Bromelain Cleavage of Octahydrolysobactin

200 µg of octahydrolysobactin are dissolved in 10 µl of methanol and then 190 µl of cleavage buffer (0.1 M sodium phosphate, 10 mM cysteine, 2 mM EDTA pH 6.5) are added. 4 µg of bromelain (1:50) are added and the reaction is carried out at 37° C. Aliquots of 30 µl are taken after 0, 0.5, 1, 3, 6 and 24 h and the enzyme cleavage is stopped with 30 µl of acetonitrile/1% TFA. The samples are stored at −20° C. until analysis.

See Table 7 for the peptide sequences of the bromelain cleavage products.

The activity of the bromelain batch used (about 4 U/mg) is checked by a control cleavage using the protein interleukin-4 double mutein Arg(121)→Asp(121)/Tyr(124)→Asp(124) (BAYER Healthcare AG, D-Wuppertal).

Example 25

Enzymatic Synthesis of Dihydrolysobactin with Chymotrypsin

800 µg of the peptide Leu-Leu-PheOMe and 100 µg of the peptide 4-11 are dissolved in 200 µl of methanol and then 200 µl of synthesis buffer (0.1 M sodium tetraborate pH 9) are added. 24 µg of chymotrypsin are added and the reaction is carried out at 37° C. Aliquots of 30 µl are taken after 0, 0.5, 1, 3, 6 and 24 h and the synthesis is stopped with 30 µl of acetonitrile/1% TFA. The samples are stored at −20° C. until analysis.

Dihydrolysobactin is detected using HPLC and CZE.

Example 26

Enzymatic Synthesis of Dihydrolysobactin Derivatives with Chymotrypsin

800 µg of the peptide Boc-Leu-Leu-PheOMe are dissolved in 200 µl of tetrachloromethane and then 200 µl of synthesis buffer (0.1 M sodium tetraborate pH 9) which contains 100 µg of the peptide 4-11 are added. 24 µg of chymotrypsin are added and the reaction is carried out at 37° C. Aliquots of 30 µl are taken after 0, 0.5, 1, 3, 6 and 24 h and the synthesis is stopped with 30 µl of acetonitrile/1% TFA. The samples are stored at −20° C. until analysis.

Dihydrolysobactin derivatives are detected by HPLC and CZE.

Example 27

Enzymatic Synthesis of Octahydrolysobactin with Chymotrypsin

800 µg of the peptide Leu-Leu-Ala(3-cyclohexyl)OMe and 100 µg of the peptide 4-11 are dissolved in 200 µl of methanol and then 200 µl of synthesis buffer (0.1 M sodium tetraborate pH 9) are added. 24 µg of chymotrypsin are added and the reaction is carried out at 37° C. Aliquots of 30 µl are taken after 0, 0.5, 1, 3, 6 and 24 h and the synthesis is stopped with 30 µl of acetonitrile/1% TFA. The samples are stored at −20° C. until analysis.

Octahydrolysobactin is detected by HPLC and CZE.

Example 28

N-Terminal Sequence Analysis 3 nmol of fragments dissolved in 60% acetonitrile/0.1% TFA are loaded onto a sequencer sheet which is preincubated with PolybrenR. The proteins are sequenced using the usual sequencer cycle. The PTH-amino acids are identified by means of online HPLC using a 40 pmol PTH standard. The non-proteinogenic amino acids are identified by their relative position to the standard amino acids. The purity of the peptides is estimated from the amino acid of the 1st PTH cycle. The various peptides are sequenced over 4 to 12 stages. Tables 1 to 7 show the protein sequences determined.

TABLE 1

Peptide sequences of the substrates

| Peptides | Determined peptide sequences of the substrate |
| --- | --- |
| 1. Dihydro-lysobactin | Leu-Leu-Phe-Leu(OH)-Leu-Arg-Ile-(allo)Thr-Gly-Asn(OH)-Ser |
| 2. Octahydro-lysobactin | Leu-Leu-PTHAla(3-cyclohexyl)*-Leu(OH)-Leu-Arg-Ile-(allo)Thr-Gly-Asn(OH)-Ser |

TABLE 2

Sequence analysis of various peptides (1-3) or peptide fragments (1-3) of the chymotrypsin cleavage

| Peptides | Deteremined peptide sequences of the chymotrypsin cleavage product |
| --- | --- |
| 1. Peptide 4-11 | Leu(OH)-Leu-Arg-Ile-(allo)Thr-Gly-Asn(OH)-Ser |
| 2. Peptide 1-3 | Leu-Leu-Phe |
| 3. Peptide 1-3 | Leu-Leu-PTHAla(3-cyclohexyl)* |

*PTHAla(3-cyclohexyl) is not detectable as a peak with the PTH system used.

TABLE 3

Sequence analysis of various peptides and peptide fragments of the subtilisin cleavage of dihydro- and octahydrolysobactin (1-4). The cleavage product 4-10 is only formed to a greater extent after 24 h.

| Peptides | Determined peptide sequences of the subtilisin cleavage product |
| --- | --- |
| 1. Peptide 4-11 | Leu(OH)-Leu-Arg-Ile-(allo)Thr-Gly-Asn(OH)-Ser |
| 2. Peptide 4-10 | Leu(OH)-Leu-Arg-Ile-(allo)Thr-Gly-Asn(OH)-Ser |
| 3. Peptide 1-3 | Leu-Leu-Phe |
| 4. Peptide 1-3 | Leu-Leu-PTHAla(3-cyclohexyl)* |

*PTHAla(3-cyclohexyl) is not detectable as a peak with the PTH system used.

TABLE 4

Sequence analysis of various peptides and peptide fragments of the thermolysin cleavage of dihydro- and octahydrolysobactin (1-3).

| Peptides | Determined peptide sequences of the thermolysin cleavage product |
| --- | --- |
| 1. Peptide 3-11 | Phe-Leu(OH)-Leu-Arg-Ile-(allo)Thr-Gly-Asn(OH)-Ser |
| 2. Peptide 3-11 | PTHAla(3-cyclohexyl)*-Leu(OH)-Leu-Arg-Ile-(allo)Thr-Gly-Asn(OH) |
| 3. Peptide 1-2 | Leu-Leu |

*PTHAla(3-cyclohexyl) is not detectable as a peak with the PTH system used.

TABLE 5

Sequence analysis of various peptides and peptide fragments of the papain cleavage of dihydro- (1, 2, 3, 4) and octahydrolysobactin (1, 2, 3, 5). Cleavage product 4-10 is only formed to a greater extent after 24 h.

| Peptides | Determined peptide sequences of the papain cleavage product |
| --- | --- |
| 1. Peptide 5-11 | Leu-Arg-Ile-(allo)Thr-Gly-Asn(OH)-Ser |
| 2. Peptide 5-9 | Leu-Arg-Ile-(allo)Thr-Gly |
| 3. Peptide 10-11 | Asn(OH)-Ser |
| 4. Peptide 1-4 | Leu-Leu-Phe-Leu(OH) |
| 5. Peptide 1-4 | Leu-Leu-PTHAla(3-cyclohexyl)*-Leu(OH) |

*PTHAla(3-cyclohexyl) is not detectable as a peak with the PTH system used

TABLE 6

Sequence analysis of various peptides and peptide fragments of the proteinase K cleavage of dihydro- (1, 2) and octahydrolysobactin (3, 4).

| Peptides | Determined peptide sequences of the proteinase K cleavage product |
| --- | --- |
| 1. Peptide 4-11 | Leu(OH)-Leu-Arg-Ile-(allo)Thr-Gly-Asn(OH)-Ser |
| 2. Peptide 5-11 | Leu-Arg-Ile-(allo)Thr-Gly-Asn(OH)-Ser |
| 4. Peptide 4-10 | Leu(OH)-Leu-Arg-Ile-(allo)Thr-Gly-Asn(OH) |
| 5. Peptide 5-10 | Leu-Arg-Ile-(allo)Thr-Gly-Asn(OH) |
| 6. Peptide 1-2 | Leu-Leu |

TABLE 7

Sequence analysis of various peptides and peptide fragments of the bromelain cleavage of open-chain lysobactin (1, 4), dihydro- (2, 4) and octahydrolysobactin (3, 4).

| Peptides | Determined peptide sequences of the bromelain cleavage product |
| --- | --- |
| 2. Peptide 1-9 | Leu-Leu-Phe-Leu(OH)-Leu-Arg-Ile-(allo)Thr-Gly |
| 3. Peptide 1-9 | Leu-Leu-PTHAla(3-cyclohexyl)*-Leu(OH)-Leu-Arg-Ile-(allo)Thr-Gly |
| 4. Peptide 10-11 | Asn(OH)-Ser |

*PTHAla(3-cyclohexyl) is not detectable as a peak with the PTH system used.

Example 29

Amino Acid Analysis

Amino acid analysis is an important qualitative and quantitative parameter for characterizing proteins. In addition to the protein content, in the case of known primary structure, the number of the individual amino acids is determined. The amino acid analysis of lysobactin derivatives and peptide fragments is in good agreement with the theoretical values from the primary structure (Table 8). Non-proteinogenic amino acids are only quantified in the presence of corresponding standards.

100 µg of the lysobactin derivatives and peptide fragments are dissolved in 200 µl of 6 N hydrochloric acid and hydrolyzed at 166° C. for 1 h. About 5 nmol of the samples are introduced into the amino acid analyzer. The amount of amino acid is determined via a 4 nmol amino acid standard.

TABLE 8

Amino acid analysis of dihydro-, octahydrolysobactin, dihydro- + octahydrolysobactin, fragment 4-11 and 1-3. The integers are based on Ile = 1 or Leu = 2.

| Amino acid | Peptide 1-3 | Theoretical numbers | Peptide 4-11 | Theoretical numbers | Dihydro- + octahydro-lysobactin | Dihydro-lysobactin | Octahydro-lysobactin | Theoretical numbers |
|---|---|---|---|---|---|---|---|---|
| Asx(OH) | | | n.d. | 1 | n.d. | n.d. | n.d. | 1 |
| Asx | | | | | | | | |
| alloTHR | | | 1.04 | 1 | 0.91 | 1.11 | 1.01 | 1 |
| Ser | | | 0.59 | 1 | 0.89 | 0.99 | 0.90 | 1 |
| Glx | | | | | | | | |
| Gly | | | 1.11 | 1 | 1.15 | 1.17 | 1.12 | 1 |
| Ala | | | | | | | | |
| Val | | | | | | | | |
| Met | | | | | | | | |
| Ile* | | | 1.00 | 1 | 1.00 | 1.00 | 1.00 | 1 |
| Leu* | 2.00 | 2 | 1.04 | 1 | 2.93 | 2.33 | 2.53 | 3 |
| Tyr | | | | | | | | |
| Phe | 1.01 | 1 | | | 0.55 | 1.08 | | 1 |
| Ala(3-cyclo-hexyl) | | | | | n.d. | | n.d. | 1 |
| Leu(OH) | | | n.d. | 1 | n.d. | n.d. | n.d. | 1 |
| Lys | | | | | | | | |
| Arg | | | 1.06 | 1 | 1.05 | 1.18 | 1.15 | 1 |
| Phe(OH) | | | | | | | | |
| Sum AS | 3.01 | 3 | 5.83 | 8 | 9.39 | 8.85 | 7.71 | |

Example 30

Reverse-phase Chromatography

Figure 1:
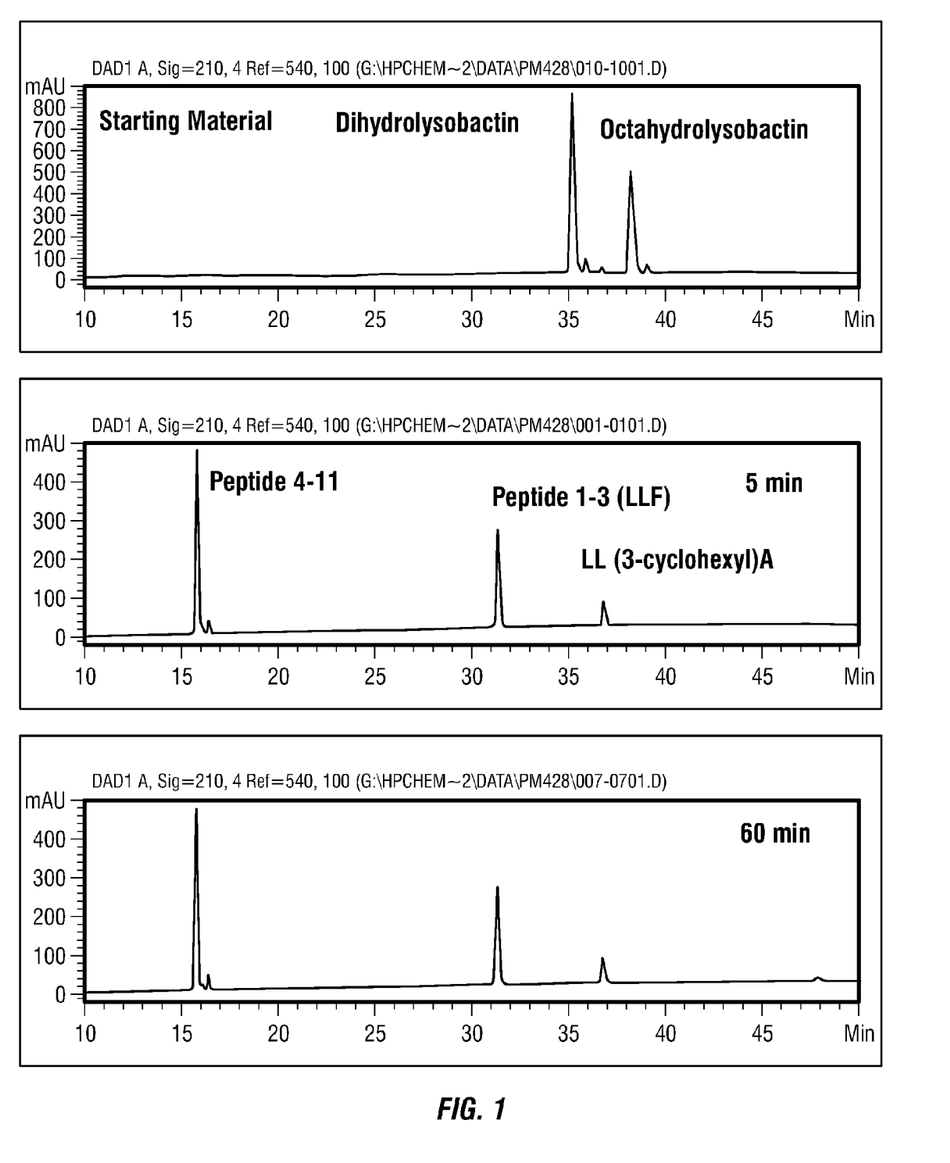
FIG. 1: Time course of a preparative enzymatic cleavage with chymotrypsin (Example 11). Superimposition of HPLC diagrams of a preparative enzymatic cleavage with chymotrypsin of a mixture of dihydro- and octahydrolysobactin. The separation conditions are as reported in the description under Example 30 (UV detection 210 nm).

In the HPLC chromatography of proteins on chemically bound reversed phases, a bond to the phase used is formed via a hydrophobic interaction of the proteins. The peptides are displaced by organic solvents (mobile phase) according to the strength of their bond to the stationary phase. For this reason, this method is a good criterion for assessing the purity of a peptide and for monitoring the rate of enzymatic cleavage and the resulting cleavage products. The peptides dihydrolysobactin and octahydrolysobactin elute from the RP-18 phase at about 35 min and about 38 min, fragment 4-11 at about 16 min, 1-3 (LLF) at about 31 min and 1-3 (LLA(3-cyclohexyl)) at about 37 min. FIG. 1 shows the time course of a preparative enzymatic cleavage with chymotrypsin (Example 11).

About 20 μg of the enzymatic cleavage products and the starting compounds dihydrolysobactin and octahydrolysobactin or the mixture are chromatographed on a Zorbax 300SB-C18 column (4.6 mm×150 mm; 3.5 μm material; 300 angstrom pore diameter). The eluent used is an acetonitrile/TFA gradient. Conditions: solvent A 0.1% TFA, solvent B 60% acetonitrile/0.1% TFA; flow 0.7 ml/min, column temperature 40° C., UV detection 210 nm, solvent A 0.1% TFA, solvent B 0.1% TFA/60% acetonitrile; gradient: 0 min 0% B, 2 min 10% B, 50 min 80% B, 52 min 100% B, 55 min 0% B, 60 min 0% B.

Example 31

Capillary Zone Electrophoresis (CZE)

Figure 2:
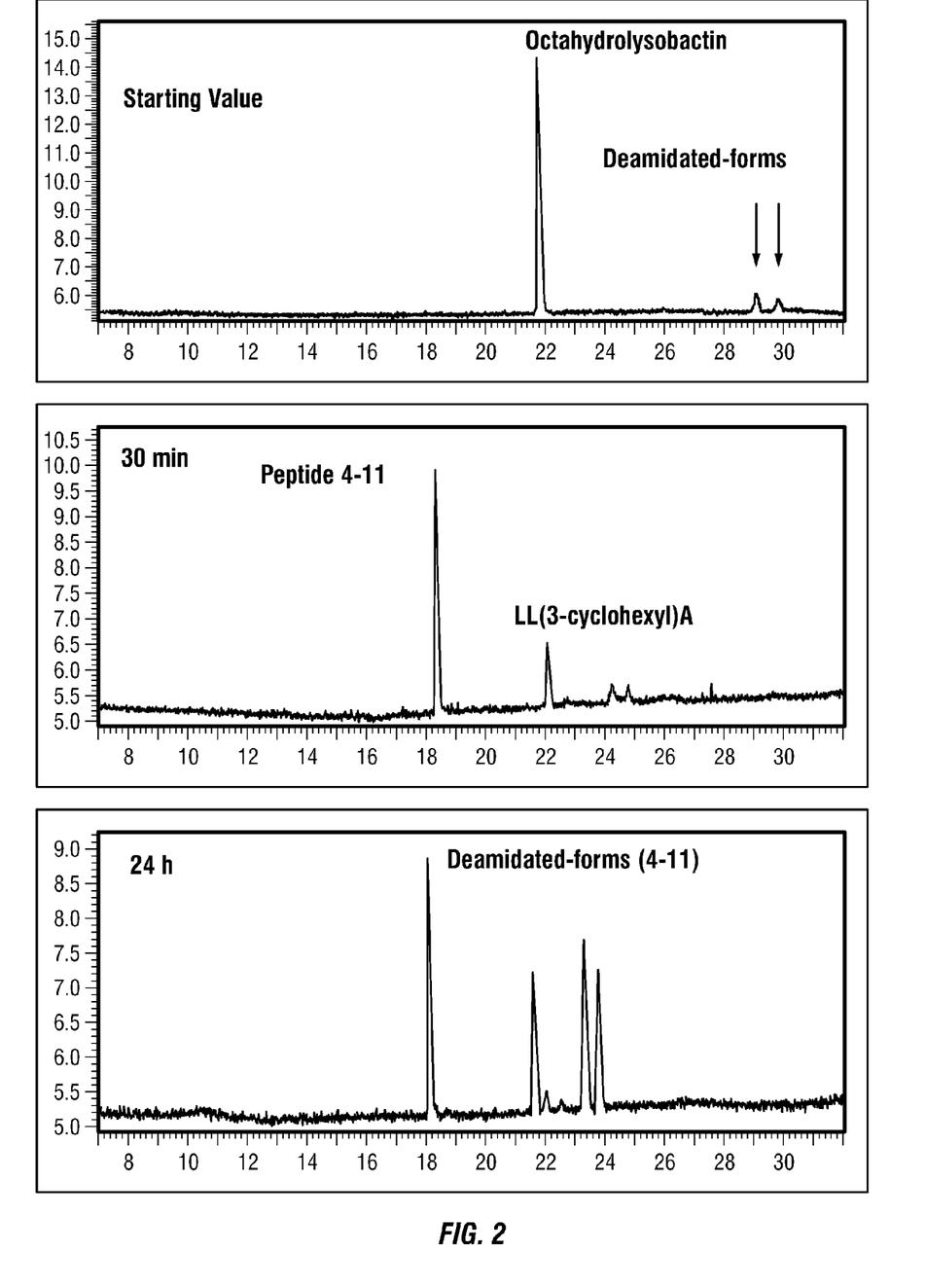
FIG. 2: Time course of an enzymatic cleavage of octahydrolysobactin with chymotrypsin (Example 5). Superimposition of CZE diagrams of an enzymatic cleavage with chymotrypsin of octahydrolysobactin. The separation conditions are as reported in the description under Example 31 (UV detection 210 nm).

Capillary electrophoresis permits the separation of peptides and proteins on the basis of their charge in an electrical field. The quality of the separation depends on the buffer, the pH, the temperature and the additives used. The capillaries used are so-called fused silica columns having an internal diameter of 50-100 μm. This method is a very good criterion for assessing the purity of a peptide and for monitoring the formation of enzymatic cleavage products. The peptides dihydrolysobactin and octahydrolysobactin elute from the capillary column at about 21 min, fragment 4-11 at about 18 min, 1-3 (LLF) at about 24 min, 1-3 (LLA(3-cyclohexyl)) at about 22 min, the deamidated forms as a double peak at about 30 min (1-11) and 24 min (4-11). FIG. 2 shows the time course of an enzymatic cleavage of octahydrolysobactin with chymotrypsin (Example 5). The great increase in deamidated products after 24 h in the buffer can clearly be seen.

About 4 ng of the enzymatic cleavage products or the starting compounds dihydrolysobactin and octahydrolysobactin, or the mixture, are investigated by means of capillary electrophoresis on a glass column (length 72 cm, internal diameter 50 μm). Conditions: current 90 μA, column temperature 25° C., 100 mM phosphate buffer pH 3.0, UV detection 210 nm, loading under pressure 3 seconds.

Example 32

Molecular Weight Determined by HPLC-ESI-MS

Peptides and enzymatic cleavage products are separated by RP-18-HPLC chromatography and the molecular weight is determined by electron spray ionization (ESI).

About 100 μg of chymotrypsin cleavage of the mixture of dihydrolysobactin and octahydrolysobactin are separated with a Zorbax C18-HPLC column under the following conditions: solvent A 0.1% TFA, solvent B 60% acetonitrile/0.1% TFA; flow 0.7 ml/min, column temperature 40° C., UV detection 210 nm, solvent A 0.1% TFA, solvent B 0.1% TFA/60% acetonitrile; gradient: 0 min 0% B, 2 min 10% B, 50 min 80% B, 52 min 100% B, 55 min 0% B, 60 min 0% B. The peptides are transferred to the atmospheric pressure ion source of the mass spectrometer and ionized there. From there the ions are transferred to the high vacuum region of the mass spectrometer and detected. Table 9 shows the molecular weights determined.

TABLE 9

Molecular weights of dihydrolysobactin, octahydrolysobactin and enzymatic cleavage products compared with the theoretical molecular weight (MW) in Dalton.

| Peptides | MW in Da | Theoretical MW in Da |
|---|---|---|
| 1. Dihydrolysobactin | 1279 | 1278.5 |
| 2. Octahydrolysobactin | 1285 | 1284.6 |
| 3. Peptide 4-11 | 905 | 905 |
| 4. Peptide 1-3 (LLF) | 391 | 391 |
| 5. Peptide 1-3 (LLA(3-cyclohexyl)) | 397 | 397 |
| 6. Peptide 1-9 | 1062 | 1061.5 |
| 7. Peptide 1-9 (A(3-cyclohexyl)) | 1068 | 1067.6 |

Example 33

Preparative Chymotrypsin Cleavage of the Mixture Dihydro/Octahydrolysobactin 18.27 g of dihydro- and octahydrolysobactin (about 5:4) are dissolved in 365 ml of methanol and diluted to 3654 ml with chymotrypsin (731 mg) and cleavage buffer. The reaction is carried out for 30 min at 37° C. and then stopped with 20 ml of TFA and 150 ml of acetonitrile. Before the addition of the enzyme, the solutions are warmed to 37° C. in a drying cabinet. Aliquots of 200 μl are taken after 0 and 0.5 h and the enzyme cleavage is stopped with 200 μl of 0.1% TFA in 30% acetonitrile/70% water. The samples are analyzed by HPLC (retention time fragment 4-11 about 3.6 min., fragment 1-3 (LLF) about 9.6 min., fragment 1-3 (LL(hexahydro)F) about 11.3 min.) (eluent A: 0.1% TFA in water, eluent B: 0.1% TFA in 60% acetonitrile/40% water, gradient: 0 min 30% B, 10 min 80% B, 11 min 100% B, 12 min 30% B, 15 min 30% B; flow: 0.7 ml/min, column temperature: 40° C., detection: 210 nm). Alternatively, method 11 is used. The solution is divided into 9×500 ml portions and frozen at −70° C. until preparative RP separation. Fragment 4-11 is isolated by preparative HPLC in several runs.

Preparative Separation of Fragments 1-3 and 4-11:

About 800 ml of the cleavage solution are filtered through a cartridge (0.2 μm) and chromatographed in two portions of about 400 ml on a Source 15RPC column (column size: 2360 ml) using a methanol/TFA gradient. Eluent A: 0.1% TFA in water, eluent B: 0.1% TFA in 100% methanol; flow: 30 ml/min.; detection 215 nm. The gradient is run according to column volumes: after application, the column is washed with 3.6 column volumes of eluent A, and then in 18 column volumes to 45% B, in 0.67 column volumes to 100% B, 1.3 column volumes 100% B, in 0.67 to 0% B, 7 column volumes of eluent A for equilibration.

10.36 g (77% of theory) of fragment 4-11 are obtained as product.

HPLC/UV-Vis (Method 4): $R_t$=0.5 min.

LC-MS (Method 1): $R_t$=1.0 min;

MS (ESIpos.): m/z (%)=453.6 (100) $[M+2H]^{2+}$, 906 (10) $[M+H]^+$.

MS (ESIneg.): m/z (%)=904 (100) $[M-H]^-$.

What is claimed is:

1. A method for preparing dihydrolysobactin, octahydrolysobactin or mixtures thereof, whereby lysobactin is converted to dihydrolysobactin, octahydrolysobactin or mixtures thereof by hydrogenolytic ring opening with hydrogen in the presence of a hydrogenation catalyst in a solvent.

2. The method of claim 1, wherein the hydrogenation catalyst is palladium.

3. The method of claim 1, wherein the solvent is an isopropanol-water mixture.

4. A method for preparing lysobactin fragment 4-11 and lysobactin fragment 1-3, whereby a compound selected from the group consisting of dihydrolysobactin, octahydrolysobactin and mixtures thereof is enzymatically cleaved to give lysobactin fragment 4-11 and lysobactin fragment 1-3.

5. The method of claim 4, wherein the enzyme is a eukaryotic serine protease or a microbial serine protease.

6. The method of claim 5, wherein the serine protease is chymotrypsin.

7. A method for preparing a compound selected from the group consisting of lysobactin fragment 3-11, lysobactin fragment 5-11, lysobactin fragment 4-10, lysobactin fragment 1-9 and mixtures thereof, whereby a compound selected from the group consisting of dihydrolysobactin, octahydrolysobactin and mixtures thereof is enzymatically cleaved to give a compound selected from the group consisting of lysobactin fragment 3-11, lysobactin fragment 5-11, lysobactin fragment 4-10, lysobactin fragment 1-9 and mixtures thereof.

8. The method of claim 7, wherein the enzyme is a metalloprotease or a cysteine protease.

* * * * *